United States Patent [19]
Colligan et al.

[11] Patent Number: 5,540,778
[45] Date of Patent: Jul. 30, 1996

[54] METHOD AND APPARATUS FOR TIPPING, CUTTING, AND SORTING SUTURES

[75] Inventors: Francis D. Colligan, Waterbury; Ronald H. Belcourt, Jr., Meriden, both of Conn.

[73] Assignee: United States Surgical Corporation, Norwalk, Conn.

[21] Appl. No.: 309,705

[22] Filed: Sep. 21, 1994

[51] Int. Cl.$^6$ ..................................................... B05C 11/00
[52] U.S. Cl. ............................. 118/672; 118/712; 118/33; 118/36
[58] Field of Search ............................... 118/672, 33, 36, 118/325, 712; 269/238, 71; 606/228; 19/43, 0.6; 28/245, 246; 427/2.31, 175, 293, 424, 117; 73/160

[56] References Cited

U.S. PATENT DOCUMENTS

| | | | |
|---|---|---|---|
| 1,920,737 | 8/1933 | Beplate | 68/276 |
| 2,402,228 | 6/1946 | Jackson et al. | 28/246 |
| 2,734,506 | 2/1956 | Nichols . | |
| 3,004,865 | 10/1961 | Schmitz | 118/325 |
| 3,736,646 | 6/1973 | Schmitt et al. . | |
| 3,849,185 | 11/1974 | Shepherd . | |
| 3,890,975 | 6/1975 | McGregor . | |
| 3,980,177 | 9/1976 | McGregor . | |
| 4,093,200 | 6/1978 | Ludvik . | |
| 4,344,382 | 8/1982 | Hausler et al. . | |
| 4,431,684 | 2/1984 | Strohmaier . | |
| 4,595,600 | 2/1986 | Keeven et al. . | |
| 4,687,827 | 8/1987 | Russo . | |
| 4,832,025 | 5/1989 | Coates . | |
| 5,007,922 | 4/1991 | Chen et al. . | |
| 5,123,912 | 6/1992 | Kaplan et al. | 606/230 |
| 5,156,788 | 10/1992 | Chesterfield et al. . | |
| 5,269,808 | 12/1993 | Proto et al. . | |

*Primary Examiner*—Brenda A. Lamb

[57] ABSTRACT

A method and apparatus for tipping, cutting, and sorting sutures includes a suture supply, a tipping station wherein delimited portions of the suture are tipped, preferably with a cyanoacrylate tipping agent, a diameter measuring station, a cutting station wherein a knife is operated to cut the suture at a tipped portion to form cut suture lengths having tipped suture ends for insertion into the barrel end aperture of a surgical needle, and a pair of graspers for alternatively grasping and drawing the suture from the suture supply through the tipping apparatus, the diameter measuring station and the cutting station. Optionally, a drying station can be interposed to hasten the curing of the tipping agent. Preferably, a controller is provided for controlling the sequence of operation of the apparatus and for controlling sorting of cut suture lengths deposited by the graspers onto a tilting sorting table.

13 Claims, 4 Drawing Sheets

METHOD AND APPARATUS FOR TIPPING, CUTTING, AND SORTING SUTURES

BACKGROUND

1. Technical Field

A method and apparatus for tipping, cutting and sorting surgical sutures is disclosed. More particularly, the present disclosure describes a method and apparatus for automating the steps of tipping, cutting and sorting surgical sutures.

2. Background of the Art

For many years, surgeons have employed needle-suture combinations in which a suture of ligature is attached to the shank end of a needle. Such needle-suture combinations are provided for a wide variety of monofilaments and braided suture materials, both absorbable and non-absorbable, e.g, catgut, silk, nylon, polyester, polypropylene, linen, cotton, and absorbable synthetic materials such as polymers and copolymers of glycolic and lactic acid.

Needle-suture combination fall into two general classes: standard, or non-detachable, needle attachment and removable, or detachable, needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the U.S. Pharmacopoeia ("USP"). As to detachable needles, the USP prescribes individual pull-out forces and average pull-out forces as measured for five needle-suture combinations. The pull-out forces for both standard and removable needle-suture attachment set forth in the USP are hereby incorporate by reference.

One typical method for securing a suture to a needle involves providing a cylindrical recess in the shank end of a needle and securing a suture therein. For examples, U.S. Pat. No. 1,558,037 teaches the addition of a cement material to a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665, 216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Insertion of sutures into a hole, recess or tube for attachment to surgical needles presents problems peculiar to suture needle combinations. Braided multifilament sutures in particular are difficult to insert into the very small aperture of a surgical needle: unless modified, they are too limp for the suture tip to be controlled for insertion and they have a tendency to "broom ", i.e., the filaments have a tendency to flare out at the cut end so that the diameter of the cut end exceeds the diameter of the needle hole. Various techniques have been employed to modify sutures to overcome the problems of limpness and brooming. One known method employs a tipping agent, which is a material used to coat the suture to stiffen the filaments and adhere them together.

Typically, a suture to be tipped is first placed under tension to reduce slack so that the suture may be maintained in a predetermined position on a frame or rack or other suture holding device. Optionally, the tension may be such as to reduce the diameter of the suture. See, Canadian Pat. No. 1,009,532. The suture is then dipped into the tipping solution and allowed to dry while under tension. The sutures are dried, for example, by being warmed in a drying oven at about 225° F. for about 10 minutes. After drying the sutures can be cut and released from tension. The process results in a tipped end on each side of a cut, with the tipping agent adhering the suture filaments to one another to prevent brooming, thereby facilitating insertion of the suture end into a needle bore. Where tension has optionally been employed to reduce the suture diameter, release of the tension will allow the suture to expand to its original diameter except at the tipped portion. This can further facilitate insertion of the end into a needle.

Tipping agents may be dissolved in solvents to form dipping solutions. By way of example, Mariotte mixture is a dipping solution comprising nylon dissolved in isopropyl alcohol. Other polymers and solvents may also be used. Gould mixture is a dipping solution comprising nylon dissolved in methanol. At least one major manufacturer of surgical needles recommends use of Mariotte mixture or Gould mixture for tipping sutures. A multitude of other tipping agents, including polymers and solvents, have been proposed. For example McGregor (U.S. Pat. No. 3,890,975) discloses coating the suture with a binding resin or adhesive. The composition may be any non-toxic adhesive composition, either organic, inorganic or a hybrid. Suitable organic materials are such natural products as starch, dextrin, asphalt, animal and vegetable proteins, natural rubber, shellac; semi-synthetic products such as cellulose nitrate and the other cellulosics, polyamides derived from dimer acids, or castor-oil based polyurethanes; and well-known synthetic resins such as vinyl-type addition polymers, both resins and elastomers, polyvinyl acetate, polyvinyl alcohol, acrylics, unsaturated polyesters, butadiene/acrylonitrile, butadiene/ styrene, neoprene, butyl robber, polyisobutylene, and polymers formed by condensation and other stepwise mechanisms, i.e., epoxies, polyurethanes, polysulfide rubbers, and the reaction products of formaldehyde with phenol, resorcinol, urea, and melamine. McGregor states that particularly preferred bonding compositions are epoxide resins and polyester resins.

Schmitt U.S. Pat. No. 3,736, 646 discloses that it is known to tip braided sutures by dipping the end of the suture in plastic such as a polymer solution in isopropyl alcohol. Schmitt suggests that for absorbable sutures an absorbable tipping agent is desirable, and proposes that a copolymer of lactic and glycolic acid dissolved in a suitable organic solvent, such as xylene or toluene, be applied to tip the suture.

Nichols U.S. Pat. No. 2,734,506 discloses a dipping solution of polymers of methacrylic acid esters in an organic solvent such as toluene, xylene acetone, ethyl acetate, methylethyl ketone, or naphtha.

Shepherd et al. U.S. Pat. No. 3,849, 185 discloses the use of an acrylic casting syrup as a tipping agent, the syrup being fully polymerized after being applied to the suture.

In addition, paraffin/hexane solution (10% paraffin) has been used as a suture coating agent as well as Arrochem (TM), a nylon resin plus methanol composition manufactured by Arrochem, Inc. of 201 Westland Farm Road, Mt. Holly, N.C. 28120, and SILASTIC (TM) Medical Adhesive (a silicon elastomer composition manufactured by Dow Coming Co.).

U.S. Pat. No. 5,269,808 to Proto et al., discloses a method and apparatus for tipping sutures which may be employed for both coated and uncoated sutures. The method described in U.S. Pat. No. 5,269,808 includes winding the suture around a drum while continuously monitoring the suture diameter in x and y directions and adjusting the tension on the suture to control the suture diameter as it is being wound. The drum is then placed in an apparatus which passes selected portions of the suture through a mist of cyanoacrylate tipping agent generated by ultrasonic atomization. The tipping agent quickly cures and the tipped portion of the suture may be cut to create a tipped end for insertion into a surgical needle to form a needle suture device.

Another method which has been employed for treating sutures involves melt fusion, as described in U.S. Pat. No. 4,832,025, issued to Coates. The suture is heated to a temperature at least high enough to "melt fuse" a portion of the outer filaments of the suture. According to Coates, such temperature is typically about 260° C. to 300°0 C. (500° F. to 572° F.). Exposure of synthetic sutures to such extreme temperatures melt fuses the filaments, and the melt fused suture portion stiffens upon cooling. Melting of the filaments has the effect of holding the filaments together when the suture is cut. It also causes stiffening of the suture which facilitates insertion of the suture end into the drilled hole of a needle. However, the melt fusion of suture has significant drawbacks.

Firstly, the melt fusion of filaments weakens the suture, whose tensile Strength is degraded in proportion to the extent of melt fusion.

Secondly, melt fusion causes an irreversible change in the filaments which result in permanent stiffening and permanent loss of tensile strength.

Thirdly, with the extreme temperatures disclosed by Coates for melt fusion an inconveniently short heating cycle is required. For example, for a size 3/0 silicone coated polyester suture heated to between 260° C. to 300° C. in a 4 mm. diameter heating tunnel, the heating time is no more than about 3 seconds. Such short heating time makes it difficult to control the process and leads to inconsistencies and variations in the melt fused tipping process.

U.S. Pat. No. 5,156,788 to Chesterfield et al., discloses a method and apparatus for tipping sutures by delimiting a portion of the suture and heating the delimited portion under predetermined time and temperature conditions to reversibly stiffen the delimited portion upon cooling. The cooled, stiffened suture portion is cut to provide a suitably stiffened, non-brooming suture tip for insertion into a needle.

Although tipped sutures prepared in accordance with the above procedures may have been used successfully, there are several drawbacks with the use of tipping solutions and melt fusing or heat tipping. The main problems relate to tipping consistency and process control. Nonuniform solvent evaporation, which may be caused by variations in the solvent, oven temperature and heating time can result in inconsistent tipping. Furthermore, the dried residue of polymer left after evaporation can flake off or develop cracks.

A further consideration pertinent to suture tipping is that sutures are often prepared with lubricant coatings such as absorbable polymers, silicone or fatty acid salts in order to increase lubricity and to improve "tie-down" performance, i.e., the ease of sliding a knot down the suture into place. Such lubricant coatings typically are incompatible with the materials and methods currently employed for tipping sutures. In particular, prior known tipping agents do not adhere well to lubricant coated sutures, which may result in inconsistent tipping or an undesirable reduction of suture-needle pull out force. The melt fusing method of tipping may destroy the lubricant coating or render it less effective in areas away from the needle.

A further consideration in attachment of sutures to needles is matching the diameter of the suture tip to the needle hole size. For some types of needle-suture attachment, e.g., swaged removable needle-suture attachment, it may be necessary to sort sutures based on a narrow range of diameter for attachment to certain needles. Typically, such sorting has been a manual task requiring an operator to measure the diameter of each cut, tipped suture and sort the sutures according to the desired needle-suture attachment to be accomplished.

It would be desirable to provide an automated apparatus and method for tipping, cutting and, if necessary, sorting sutures.

SUMMARY OF THE DISCLOSURE

An apparatus and method are provided herein for tipping, cutting, and sorting multifilament surgical sutures. The system includes a suture feed mechanism, such as rollers, for linearly moving a suture from a supply reel through a series of processing stations. The first processing station is a tipping station wherein a predetermined portion of the suture is tipped with a tipping agent. Preferably, the tipping agent is monomeric cyanoacrylate, although any suitable tipping agent or method may be used. Optionally, the suture may be then passed through a drying station to hasten the curing of the tipping agent. Also, the suture may optionally then be passed through a measuring station in which the suture diameter is measured in orthogonal X and Y directions for quality control purposes and/or sorting, if desired. The diameter is preferably measured with a laser micrometer which may also optionally be used to adjust tensioning of the suture to control suture diameter during tipping. The suture is then grasped by mobile gripping units which pull the suture and hold it firmly while positioning it for cutting. A cutting apparatus, such as a knife blade or scissors, is then operated to cut the suture at the tipped portion, thereby creating at least one, and preferably two, tipped ends. The severed length of suture may then be sorted based upon diameter data previously gathered. Preferably, the suture feed mechanism, tipping, cutting and sorting operations are controlled by a computer, such as a microprocessor, such that the sorting operation, for example, may be controlled based upon diameter data collected at an earlier operating station.

DETAILED DESCRIPTION OF PREFERRED EMBODIMENT(S)

Figure 1:
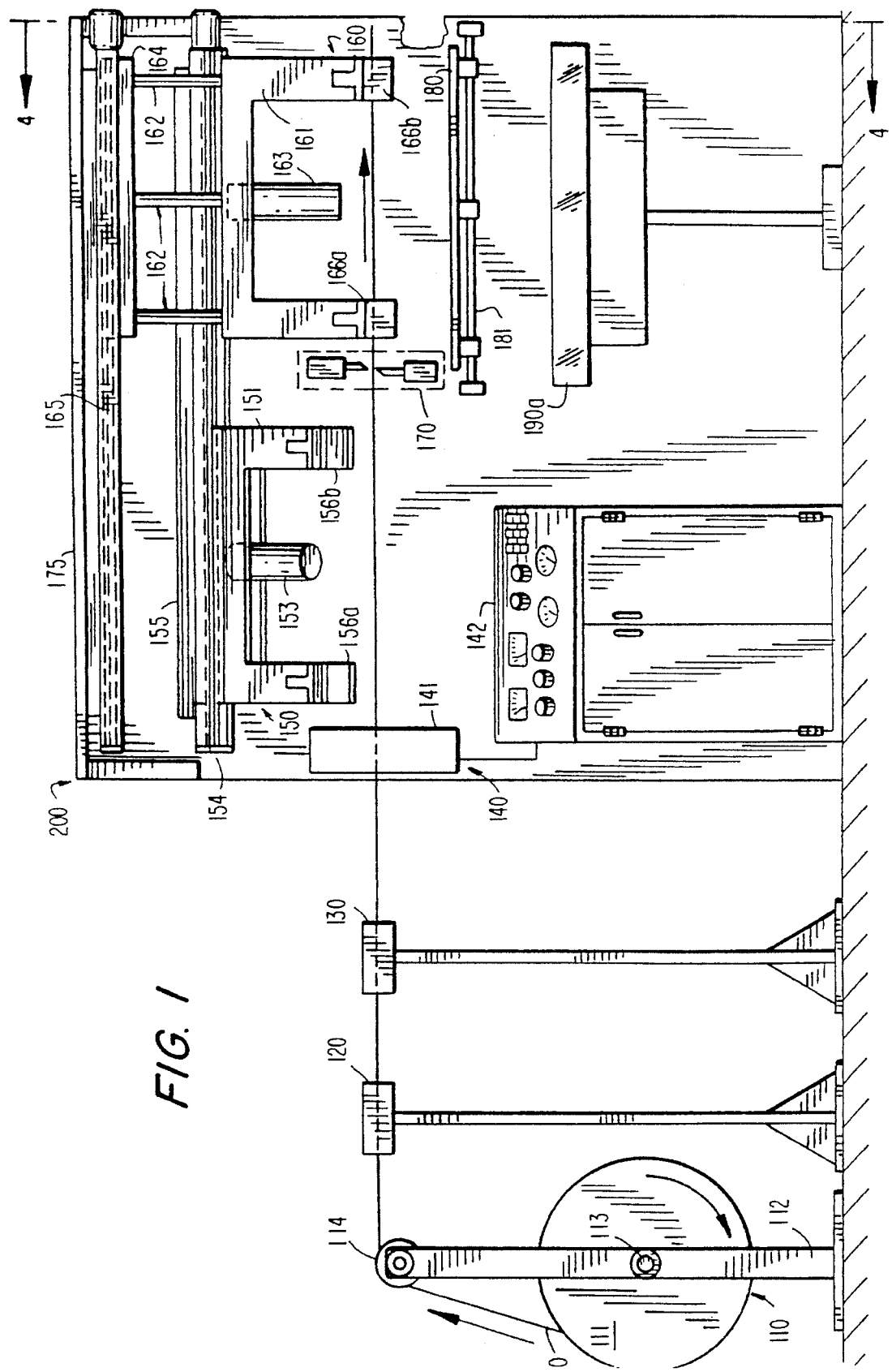
FIG. 1 is a front elevational view of the apparatus and system of the present invention.
Figure 2:
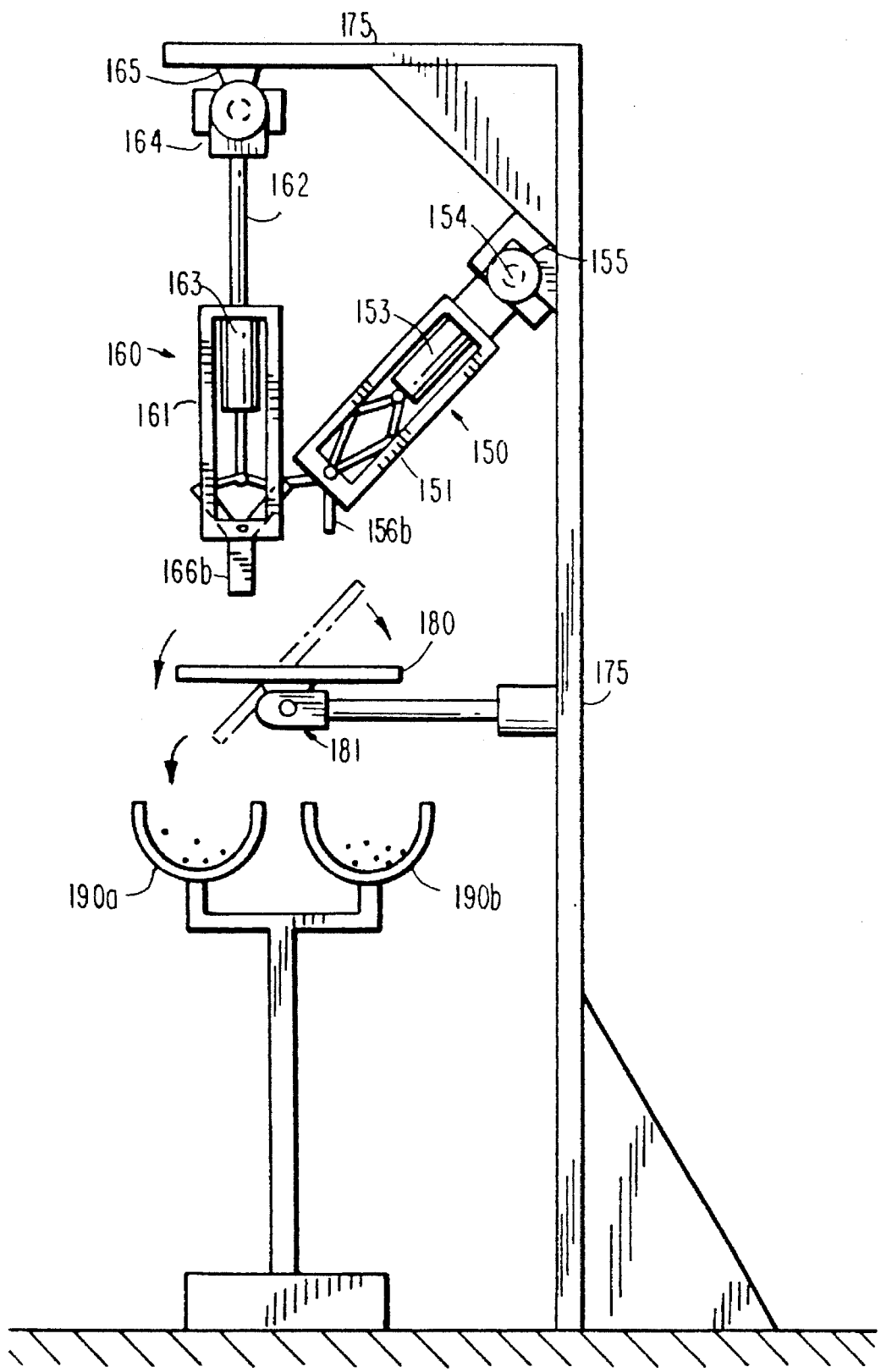
FIG. 2 is a side elevational view of the housing with suture grippers, sorting platform and suture receiving bins.

Referring to the drawings, the present method and apparatus tip, cut and sort sutures, especially multifilament braided sutures. As used herein, the term "braided" means a strand formed by crossing a number (at least three) of individual yarns composed of one or more filaments diagonally in such manner that each strand passes alternatively over and under one or more of the others. The braid may be of traditional tubular braid construction or spiroid braid construction and may include a core section composed of one or more filaments around which the braid is externally fabricated. Suitable braid constructions are disclosed, for example, in U.S. Pat. Nos. 5,261,886; 5,059,213; 5,019,093; 3,565,077; and 3,187,752. While the present disclosure is most specifically directed to tipping, cutting and sorting multifilament braided sutures, it is contemplated that the apparatus and method may find use in cutting and sorting monofilament sutures as well.

The suture can be fabricated from a wide variety of natural and synthetic fibrous materials. Such materials include non-absorbable as well as partially and fully bio-absorbable (i.e., resorbable) natural and synthetic fiber-forming polymers. Non-absorbable materials which are suitable for fabricating sutures include silk, polyamides, polyesters such as polyethylene, polypropylene, silk, cotton, linen, etc. Carbon fibers, steel fibers and other biologically acceptable inorganic fibrous materials can also be employed. Bio-absorbable sutures may be fabricated from natural collagenous material or synthetic resins including those derived from glycolic acid, glycolide, lactic acid, lactide, dioxanone, polycaprolactone, epsilon-caprolactone, trimethylene carbonate, etc., and various combinations of these and related monomers. Sutures prepared from resins of this type are known in the art. See, e.g., U.S. Pat. Nos. 3,297,033; 3,297,033; 3,839,297; and 4,429,080.

Braided multifilament sutures typically are coated with one or more coating compositions to improve functional properties such as surface lubricity and knot tie-down behavior. A variety of suture coating compositions proposed for either or both of these purposes are well known in the art, e.g., those disclosed in U.S. Pat. Nos. 3,867,190; 3,942,532; 4,047,533; 4,452,973; 4,624,256; 4,649,920; 4,716,203; 4,826,945, 4,994,074; 5,123,912, and 5,312,437.

Absorbable braided sutures may also contain a storage stabilizing amount of a filler material containing at least one water soluble liquid polyhydroxy compound and/or ester thereof. In addition to having an enhanced degree of storage stability, a braided suture which has been filled with a storage stabilizing amount of, e.g., glycerol, exhibits better flexibility and "hand" characteristics than the untreated suture. Suitable filling compositions are disclosed in U.S. Pat. Nos. 5,051,272 and 5,037,429. Moreover, since the polyhydroxy compounds are generally capable of dissolving a variety of medico-surgically useful substances, such as therapeutic agents can be used as vehicles to deliver such substances to a wound or surgical site at the time the suture is introduced into the body.

As stated, a braided suture may be impregnated with one or more medico-surgically useful substances, e.g., those which accelerate or beneficially modify the healing process when the suture is applied to a wound or surgical site. So, for example, the braided suture herein can be provided with a therapeutic agent which will be deposited at the sutured site. For example, a therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or more biologically active materials known to achieve either or both of these objectives can be applied to the braided suture of the present invention. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system, and so forth.

Cyanoacrylate is preferred ms the tipping agent. The cyanoacrylate is applied as a monomer. It possesses the advantage of substantially instantly polymerizing and bonding the filaments of the suture, even when the suture has been coated and filled with various coating and filling agents. The preferred cyanoacrylate is available under the name LOCTITE™ Medical Device Adhesive from the Loctite Corporation of Newington, Conn., and comprises 99+% ethyl cyanoacrylate and small amounts of hydroquinone and organic anhydride. The cyanoacrylate monomer can be applied to the suture in a variety of ways, such as dipping or brushing. Preferably, the cyanoacrylate is applied by spraying. An ultrasonic atomizer may be used to generate a mist of cyanoacrylate monomer, through which the suture is longitudinally passed. A novel method and apparatus for spraying cyanoacrylate monomer in the form of a mist, and passing the suture through the mist is described in U.S. Pat. No. 5,269,808.

Upon contact of the cyanoacrylate with the suture the residual moisture content of the suture and the surrounding environment catalyzes the polymerization of the cyanoacrylate almost instantly without any additional drying or curing steps being required, thereby reducing processing steps and producing a substantially complete polymerized tipping coating at the end of the apparatus cycle. The polymerized cyanoacrylate stiffens the segment of the suture by coating the individual filaments of the suture with a relatively stiff film, and, because the cyanoacrylate is an adhesive, the individual filaments are bonded together to prevent brooming.

Referring now to FIG. 1, the apparatus and method for tipping, cutting, and sorting sutures are diagrammatically illustrated. The apparatus and method have several features which are initially outlined and described in further detail below:

1. A suture supply 110;

2. A suture tipping station 120;

3. A suture drying station 130 (optional);

4. A suture diameter measuring station 140 (optional);

5. Movable suture gripping arms 150, 160; and

6. A suture cutting station 170.

The suture supply 110 preferably is a reel or spool 111 on which a length of suture 10 is wound. Roller 111 is mounted on frame 112 and pivots around axle 113 as the suture 10 is drawn off. The suture 10, after being drawn off the supply reel 111, passes around roller 114 and through tipping station 120. A predetermined amount of tension may be applied to the suture to reduce its diameter. For example, roller 114 may be regulated by means of a friction clutch to apply tension to the suture against a pulling force of grippers 150, 160, discussed below. Optionally, the clutch may apply sufficient tension to reduce the diameter of the suture against the tension applied by grippers 150, 160. When the clutch is relaxed the diameter of the suture expands. A portion of the suture is tipped at tipping station 120 by being exposed to a tipping agent such as a mist of cyanoacrylate monomer which is atomized by an ultrasonic spray head. Preferably, dry nitrogen carries the cyanoacrylate through the spray head and prevents premature drying inside the apparatus. The cyanoacrylate adheres to the filaments of multi filament sutures and bonds them together. One suitable apparatus is disclosed in U.S. Pat. No. 5,269,808. As will be appreciated, other methods of tipping may be used at tipping station 120.

The apparatus optionally may include a drying station 130, where curing of the tipping agent is promoted. For moisture-curing cyanoacrylate the drying station may be a humidifier to cure cyanoacrylate monomer on the suture. If a tipping agent other than cyanoacrylate is used, drying station 130 could apply heat, air, moisture, ultraviolet light, etc. as appropriate to cure the tipping agent.

The apparatus optionally may also include a diameter measuring station 140. The diameter measuring station 140 preferably includes a laser micrometer 141 which continuously measures the suture diameter in X and Y directions. The X and Y directions are mutually orthogonal, and orthogonal to the lengthwise orientation of the suture. A control panel 142 registers the measured diameter and optionally adjusts the tensioning for control of the suture diameter as explained in detail below. A laser micrometer suitable for use in the present invention is available from Zumbach Electronics Corp. of Mt. Kisco, N.Y. under the designation ODAC 19M, which is a microcomputer controlled measuring system having X-Y heads which incorporate laser scanners.

The apparatus also includes a cutting and sorting station 200. Referring now to FIGS. 1 to 6, portions of suture 10 are alternatively grasped by grippers 150 and 160 to draw a length of suture from reel 111 through stations 120, 130, 140 for cutting and sorting.

Grippers 150 and 160 each have a frame, 151 and 161, respectively. The frames are slidably mounted along shafts 152 and 162, respectively, and are reciprocatingly moved along the respective shafts 152, 162 by motors 153 and 163, respectively. The shafts 152 and 162 are preferably oriented in a direction substantially transverse to the running length of the suture and are fixedly mounted to respective carriages 154 and 164, respectively, which ride along rails 155 and 165 respectively. Each gripper 150 and 160 includes at least two pairs of jaws 156a/156b and 166a/166b, respectively, for grasping suture 10. Jaws 156a/156b, 166a/166b have suitable gripping surfaces to grasp and hold the suture with sufficient tension to prevent slippage but do not damage the suture. Suitable jaw surfaces include foam rubber.

The grippers 150 and 160 alternately grip and pull the suture 10 into position for cutting. For example, FIG. 1 illustrates the positioning of the graspers 150 and 160 after the suture length has been grasped and pulled by grasper 160 to the right (as shown), with grasper 150 removed from contact with the suture.

The sequence of operation of the apparatus will now be explained with reference to FIGS. 1 and 3–6.

Figure 3:
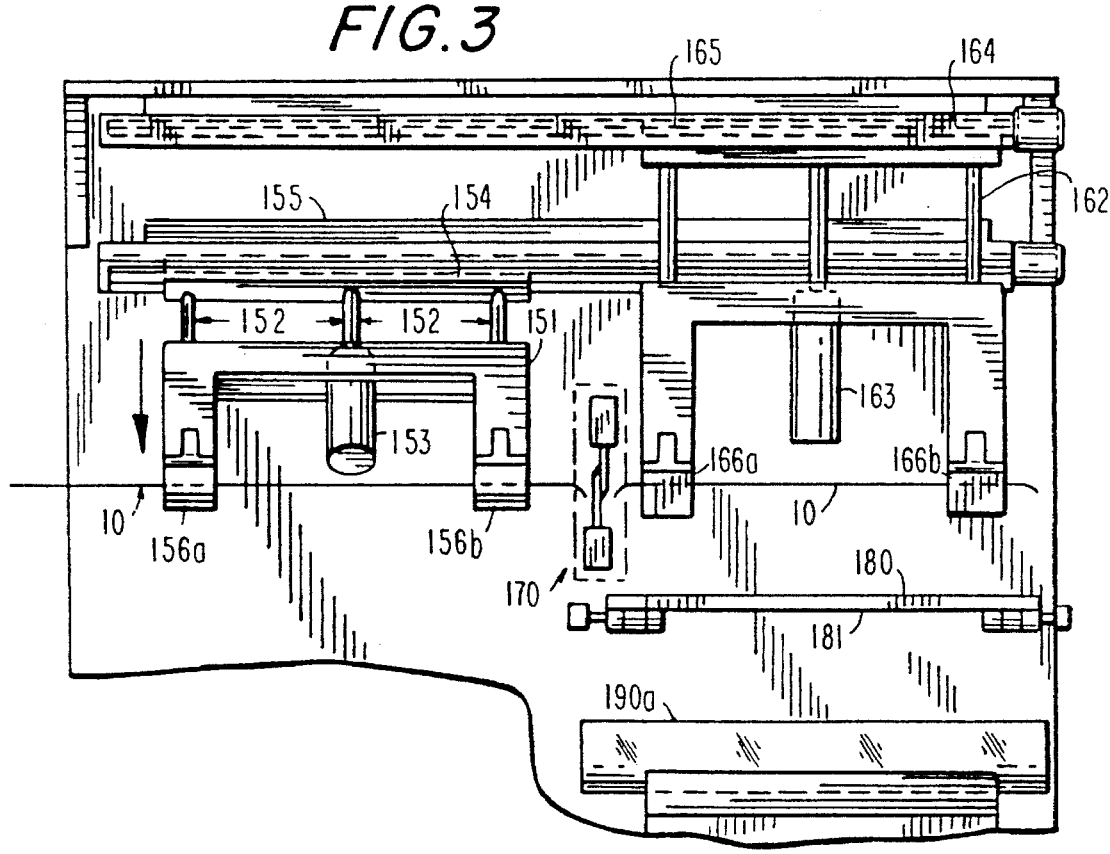
FIGS. 3 to 6 illustrate the operational sequence of pulling, positioning, cutting, and sorting sutures.
Figure 4:
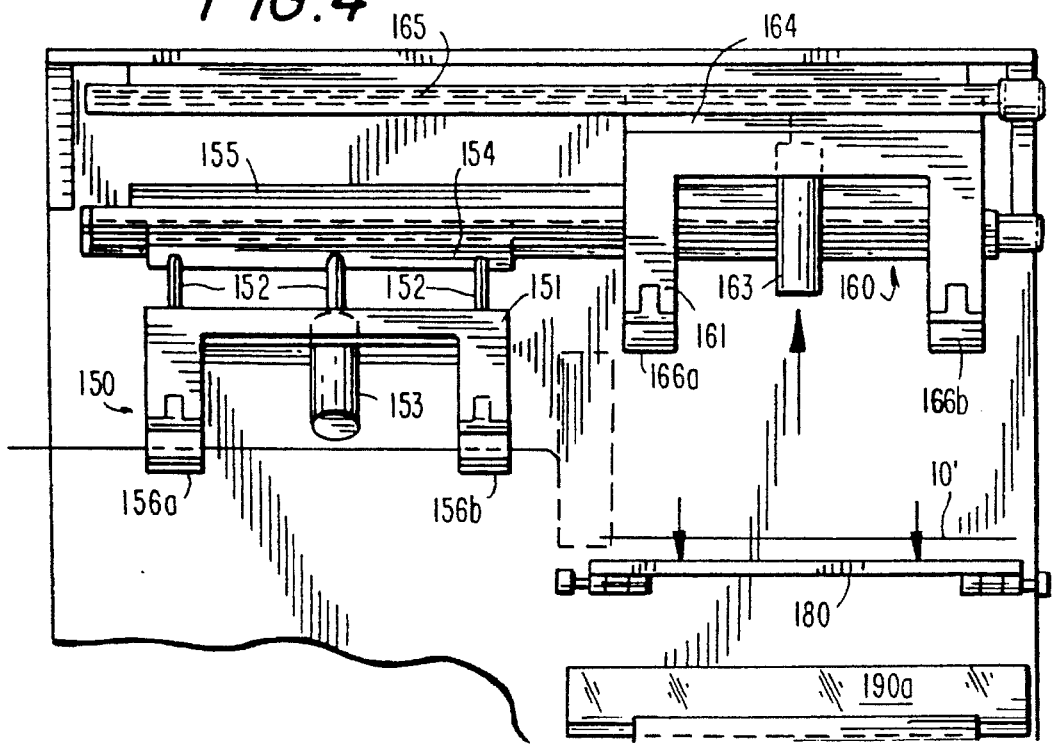

Referring to FIG. 1, grasper 150 is positioned away from suture 10 and grasper 160 has drawn suture 10 to the right. As shown in FIG. 3, grasper 150 is moved by motor 153 along rails 152 away from carriage 154 with jaws 156a, 156b in an open position. With jaws 156a, 156b positioned about suture 10 the jaws are closed to apply sufficient tension to grasp the suture without damaging the suture. The cutting apparatus 170 includes at least one knife blade and preferably two opposing knife blades which are slidably mounted to housing 175. After jaws 156a/156b have grasped suture 10 cutting apparatus 170 is activated to cut suture 10 at a tipped portion disposed between jaws 156b and 166a so that the length of suture held by grasper 160 is released from the length of suture 10. As shown in FIG. 4, the length of suture 10' cut from suture 10 and held by grasper 160 is placed on sorting table 180 by opening jaws 166a/166b for sorting in a manner to be explained below. Grasper 160 is then withdrawn from suture along rails 162 by motor 163.

Figure 5:
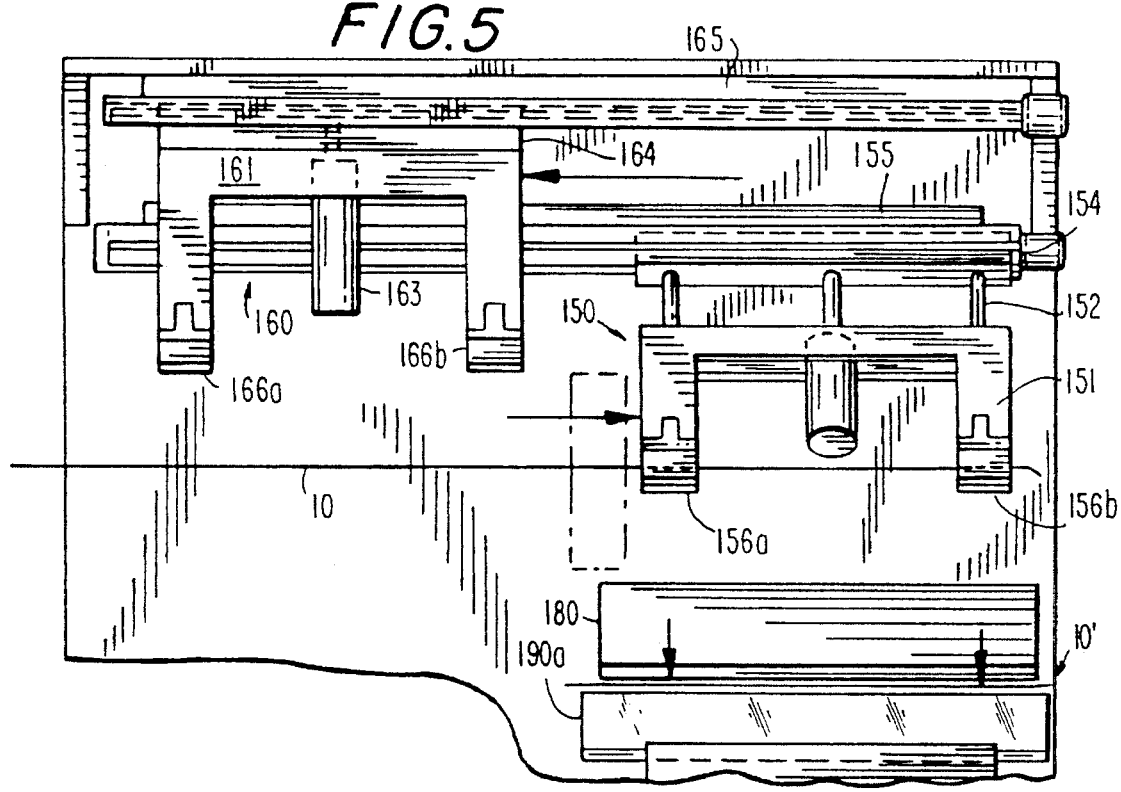

Referring to FIG. 5, grasper 150 is moved to the right along rail 155 and grasper 160 is moved to the left along rail 165. Grasper 150 is drawn to the right a sufficient distance to position a desired length of suture held by grasper 150 to the right of cutting station 170. Of course, as grasper 150 is moved to the right, suture 10 is drawn off spool 111 until the next suture portion to be tipped is positioned at tipping station 120 and a tipped suture portion is positioned at cutting station 170.

As shown in FIG. 5, table 180 is shown tilted to deposit 10' in bin 190a in a sorting operation to be explained in greater detail below. Also see FIG. 2.

Figure 6:
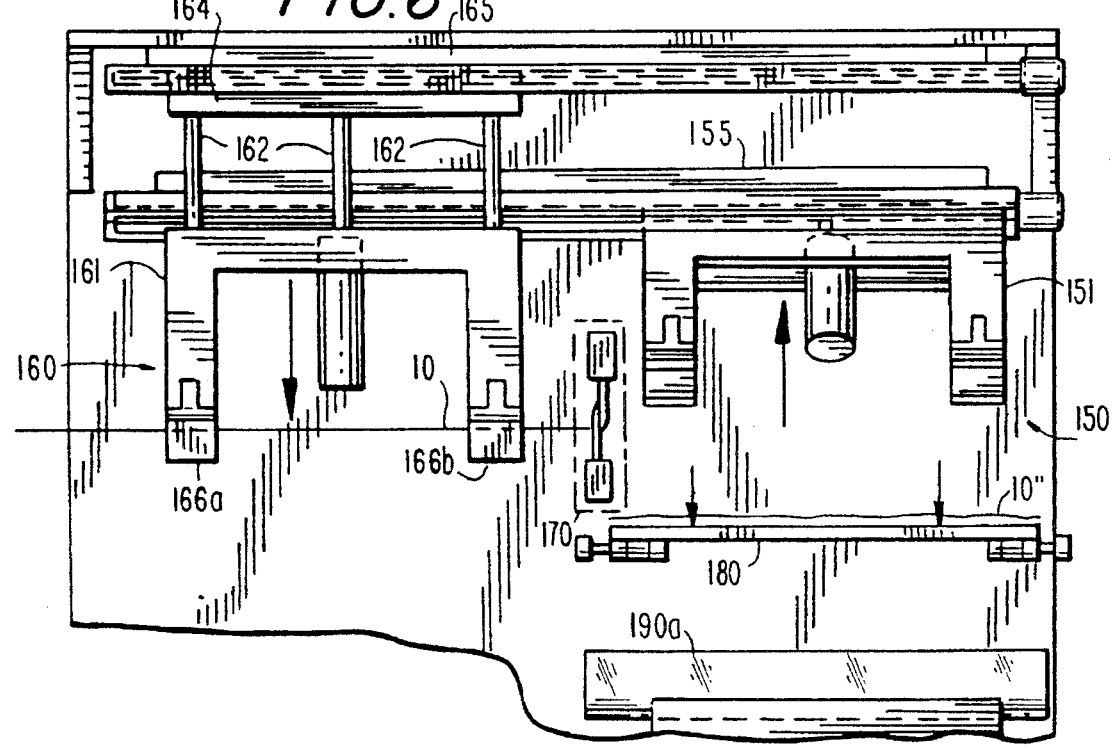

Referring now to FIG. 6, grasper 160 moves adjacent suture 10 and jaws 166a/166b are closed to grasp the suture. The next tipped suture portion is then cut at cutting station 170. Grasper 150 deposits cut length 10" onto table 180 (which has returned to a level position) by opening jaws 156a/156b adjacent the table. The foregoing steps are then repeated, alternating the positions of graspers 150, 160 to draw suture material from spool 111 to the tipping station, through the optional drying station, to the diameter measuring station and to the cutting station. The distance travelled by graspers 150, 160 may be adjusted so that a desired suture length is cut.

Controller 142 preferably controls the sequence of positioning of graspers 150, 160, the opening and closing of jaws 156a/156b, 166a/166b, activation of the tipping apparatus and drying station, and the cutting apparatus at cutting station 170. Thus, referring to FIG. 1, controller 142 has caused grasper 160 to pull suture 10 from spool 111 and grasper 150 to move to the left. Before the suture is drawn further to the right, tipping station 120 is activated to tip a portion disposed therein. In addition, diameter measuring station 140 is activated to measure the diameter of suture 10 adjacent the position to be grasped by grasper 150. As grasper 150 draws the suture to the right in the next sequence of operation, optional drying station 130 is activated to cure the tipping agent on the suture. If necessary, the advancement of the suture may be suspended with the tipped portion in the drying station for a sufficient period to cure the tipping agent. Similarly, the distance travelled by the grasper, and the length of time a given portion of the suture resides at the tipping station, drying station or diameter measuring station may be adjusted via controller 142, as appropriate.

Controller 142 stores in memory the diameter of the suture portion to be grasped by grasper 150. After the length of suture has been drawn to the right, cut from the continuous suture feed, and deposited on table 180 by grasper 150, controller 142 directs sorting of the length of suture based on the diameter measurement. Thus, referring to FIG. 2, table 180 is pivotally mounted about an axis of rotation 181, and the rotation of table 180 is controlled by a motor under the control of controller 142. A pair of suture length receiving bins 190a, 190b are disposed under and to either side of table 180. Depending upon the diameter measurement stored in controller 142, table 180 is caused to tilt to the right or left (as shown) to deposit the suture length in one of bins 190a, 190b. The determination bins into which the suture length is deposited may be made on the basis of a single accept/reject basis or to cull suture lengths of a more narrow diameter range for use in particular suture attachment process, such as attachment of removable needle-sutures. For example, sutures may be sorted so that sutures of a narrow diameter range are culled for use in removable needle-suture combinations.

While the above description contains may specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto. By way of example only, it is contemplated that the diameter measuring station and sorting stations could be omitted, or other configurations of the various stations and their sequence of operation could be made. In addition, it is contemplated that the tip of the cut, tipped suture to the right of the grasper position could be inserted dim fly into a needle attachment apparatus, such as the apparatus of U.S. application Ser. No. 07/959, 114 or 08/100,716 for attachment to a needle while under the control of a suture grasper, with the attached suture-needle combination sorted or placed directly into a bin or onto a conveyor for further processing.

What is claimed is:

1. A system for treating a multifilament suture which comprises:
   a) a supply of suture material;
   b) a tipping apparatus for tipping a suture by applying a tipping agent to a delimited portion of the suture passed longitudinally through the tipping agent;
   c) a pair of grippers each having at least one suture grasping jaw, the grippers being movable within a housing to alternately grasp and move the suture, wherein each gripper comprises a frame slidably mounted to a shaft and reciprocatingly movable along the shaft in a direction transverse to the orientation of the suture, and a carriage to which the shaft is fixedly mounted; and
   d) a cutting apparatus;
   whereby the grippers alternately grasp a length of suture and draw the suture from the suture supply through the tipping apparatus, the tipping apparatus tipping delimited portions of the suture longitudinally passed through the tipping agent, the cutting apparatus cutting the tipped delimited portions of the suture to provide cut, tipped suture lengths.

2. The system of claim 1 wherein the carriage is slidably mounted to a rail in the housing, the rail being oriented in a direction substantially parallel to the orientation of the suture.

3. The system of claim 2 wherein the at least one jaw comprises a pair of jaws spaced apart from each other, the pair of jaws being movable between open and closed configurations.

4. The system of claim 1 wherein the tipping agent is monomeric cyanoacrylate.

5. The system of claim 4 wherein the tipping apparatus includes a sprayer for spraying the cyanoacrylate tipping agent.

6. The system of claim 5 wherein the sprayer includes an ultrasonic atomizer.

7. The system of claim 1 further including a curing apparatus for promoting curing of the tipping agent applied to the tipped delimited portion of the suture after the suture has passed through the tipping agent.

8. The system of claim 1 further including a suture diameter measuring device to continuously monitor the diameter of the suture in X and Y orientations.

9. The system of claim 8 wherein the suture diameter measuring device comprises a laser micrometer.

10. The system of claim 8 wherein the suture supply includes a suture spool regulated by a friction clutch to apply tension to the suture.

11. A system for treating a multifilament suture which comprises:
    a) a supply of suture material;
    b) a tipping apparatus for tipping a suture by applying a tipping agent to a delimited portion of the suture passed longitudinally through the tipping agent;
    c) a pair of grippers each having at least one suture grasping jaw, the grippers being movable within a housing to alternately grasp and move the suture; and
    d) a cutting apparatus;
    whereby the grippers alternately grasp a length of suture and draw the suture from the suture supply through the tipping apparatus, the tipping apparatus tipping delimited portions of the suture longitudinally passed through the tipping agent, the cutting apparatus cutting the tipped delimited portions of the suture to provide cut, tipped suture lengths,
    wherein said system further includes a suture measuring device to continuously monitor the diameter of the suture in X and Y orientations, and a controller and a sorting table to sort the cut sutures based on diameter.

12. A system for treating a multifilament suture which comprises:
    a) a supply of suture material;
    b) a tipping apparatus for tipping a suture by applying a tipping agent to a delimited portion of the suture passed longitudinally through the tipping agent;
    c) a pair of grippers each having at least one suture grasping jaw, the grippers being movable within a housing to alternately grasp and move the suture; and
    d) a cutting apparatus;
    whereby the grippers alternately grasp a length of suture and draw the suture from the suture supply through the tipping apparatus, the tipping apparatus tipping delimited portions of the suture longitudinally passed through the tipping agent, the cutting apparatus cutting the tipped delimited portions of the suture to provide cut, tipped suture lengths, and wherein the cutting apparatus comprises a knife slidably mounted to the housing.

13. A system for providing cut lengths of suture comprising:
    a) a supply of suture material;
    b) a tipping apparatus for tipping a suture by applying a tipping agent to a delimited portion of the suture passed longitudinally through tipping agent;
    c) a pair of grippers each having at least one suture grasping jaw, the grippers being movable to alternatively grasp and move the suture; and
    d) a cutting apparatus;
    whereby the grippers alternately grasp a length of suture and draw the suture from the suture supply, the cutting apparatus cutting the suture into predetermined lengths, and said system further comprising a sorting apparatus to sort cut suture lengths based on diameter.

* * * * *